United States Patent
Sung et al.

(10) Patent No.: US 9,861,262 B2
(45) Date of Patent: Jan. 9, 2018

(54) CATHETER USING OPTICAL FIBER AND CAMERA

(71) Applicant: META BIOMED CO., LTD., Chungcheongbuk-do (KR)

(72) Inventors: Jae Hwan Sung, Yongin-si (KR); Ki Sub Kim, Cheongju-si (KR)

(73) Assignee: META BIOMED CO., LTD., Cheongwon-gun, Chungcheongbuk-do (KR)

( * ) Notice: Subject to any disclaimer, the term of this patent is extended or adjusted under 35 U.S.C. 154(b) by 67 days.

(21) Appl. No.: 14/425,318

(22) PCT Filed: Aug. 27, 2013

(86) PCT No.: PCT/KR2013/007665
§ 371 (c)(1),
(2) Date: Mar. 2, 2015

(87) PCT Pub. No.: WO2014/035114
PCT Pub. Date: Mar. 6, 2014

(65) Prior Publication Data
US 2015/0223671 A1    Aug. 13, 2015

(30) Foreign Application Priority Data

Sep. 3, 2012 (KR) ........................ 10-2012-0097257

(51) Int. Cl.
*A61B 1/04* (2006.01)
*A61B 1/00* (2006.01)
(Continued)

(52) U.S. Cl.
CPC ........ *A61B 1/00096* (2013.01); *A61B 1/0008* (2013.01); *A61B 1/0011* (2013.01);
(Continued)

(58) Field of Classification Search
CPC ........ A61M 25/0147; A61M 2025/015; A61M 2025/0037; A61M 25/0032; A61M 25/003; A61M 25/0023; A61B 1/0057; A61B 1/05; A61B 1/051; A61B 1/0055; A61B 1/0008; A61B 1/005; A61B 1/012; A61B 1/00105; A61B 1/00071; A61B 1/00064
(Continued)

(56) References Cited

U.S. PATENT DOCUMENTS

| 5,396,880 A | 3/1995 | Kagan et al. |
| 5,431,168 A | 7/1995 | Webster, Jr. |

(Continued)

FOREIGN PATENT DOCUMENTS

KR    10-2012-0013930 A    2/2012

*Primary Examiner* — Alexandra Newton
(74) *Attorney, Agent, or Firm* — Novick, Kim & Lee, PLLC; Jae Youn Kim (57) ABSTRACT

The present invention relates to a catheter using an optical fiber and a camera, into which the camera for lighting and the optical fiber for lighting are built so that the camera can be used during an internal examination and treatment amid irradiation of light by the optical fiber. According to the present invention, the diameter of a shaft can be minimized while forming a hole in the shaft for the camera, the optical fiber, a wire, and medicine to be inserted, and the camera, the optical fiber, and a distal end of a medicine injection tube are driven at the same time and in the same manner following the driving of the wire so that internal imaging, light irradiation, and medicine injection can be performed with accuracy.

8 Claims, 8 Drawing Sheets

(51) Int. Cl.
*A61M 25/01* (2006.01)
*A61B 1/015* (2006.01)
*A61B 1/07* (2006.01)
*A61B 1/005* (2006.01)
*A61B 1/05* (2006.01)
*A61B 1/313* (2006.01)

(52) U.S. Cl.
CPC .......... *A61B 1/0052* (2013.01); *A61B 1/0057* (2013.01); *A61B 1/00073* (2013.01); *A61B 1/00114* (2013.01); *A61B 1/00128* (2013.01); *A61B 1/00137* (2013.01); *A61B 1/015* (2013.01); *A61B 1/051* (2013.01); *A61B 1/07* (2013.01); *A61B 1/3135* (2013.01); *A61M 25/0147* (2013.01)

(58) Field of Classification Search
USPC .................................. 600/139–150, 128–130
See application file for complete search history.

(56) References Cited

U.S. PATENT DOCUMENTS 5,438,975 A * 8/1995 Miyagi .............. A61B 1/00071
600/109
6,146,355 A 11/2000 Biggs
6,447,445 B1 * 9/2002 Hirano ................. A61B 1/0008
600/129

* cited by examiner

CATHETER USING OPTICAL FIBER AND CAMERA

TECHNICAL FIELD

The present invention relates to a catheter, and more particularly, to a catheter using an optical fiber and a camera, in which the camera for lighting and the optical fiber for lighting are built-in so that the camera can be used for an internal examination and treatment amid irradiation of light by the optical fiber.

BACKGROUND ART

A catheter, in a broad sense, is defined as a tube inserted into a body for treatment.

The catheter may be classified into an endoscope-type catheter having a photographing device such as a camera to examine an inner part such that an internal organ may be examined, a catheter having a drug supplying tube to supply a drug to the internal organ, a catheter to burn and remove a tumor, etc. by irradiating a laser to the internal organ and a rotating catheter having a bendable end part for treating a intervertebral disk, etc.

Figure 1:
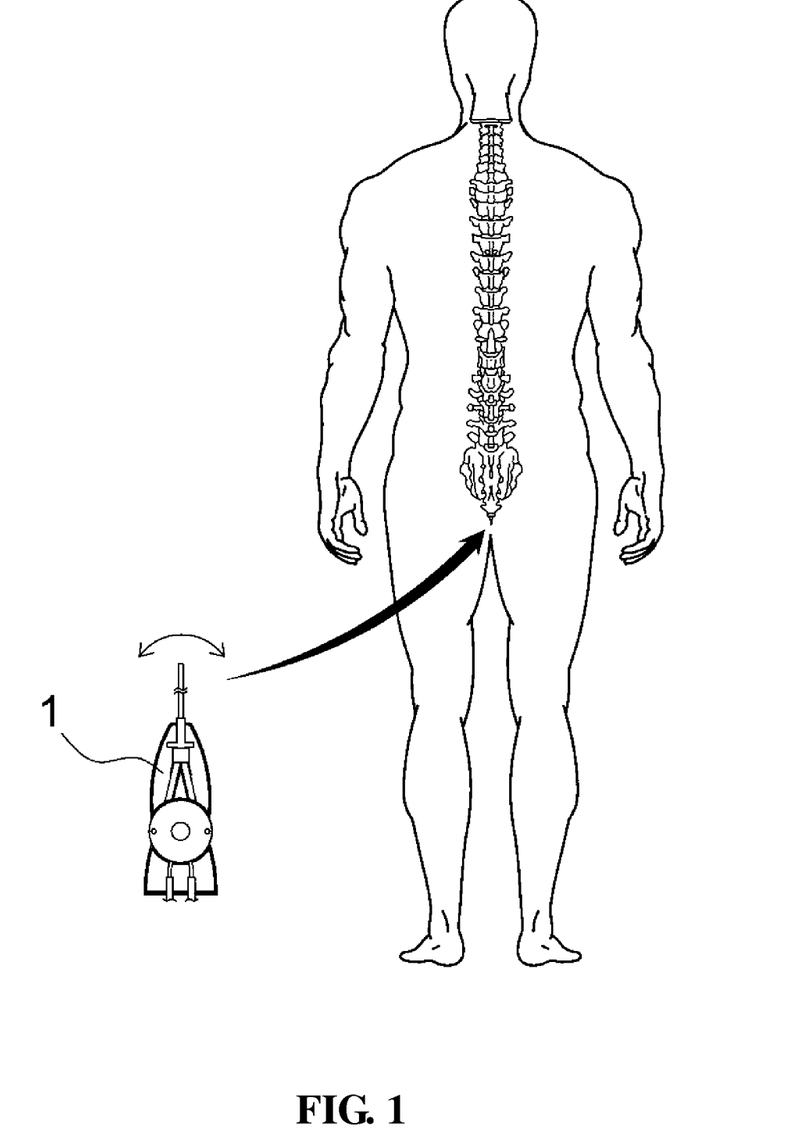
FIG. 1 is a schematic view illustrating a catheter for disk treatment in use.
Figure 2:
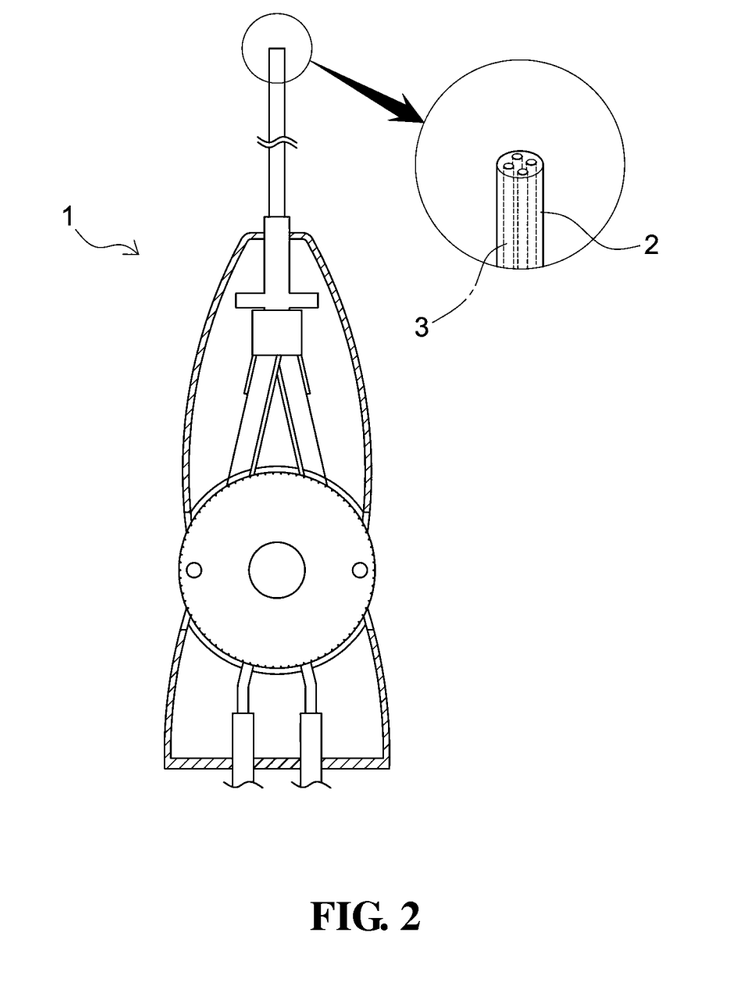
FIG. 2 is a cross sectional schematic view illustrating an embodiment of a typical catheter.

For a technology related to the catheter, a technology having a tube to supply drugs, a wire to rotate a shaft, a driving device to rotate the shaft by pulling the wire is disclosed in FIG. 2a and FIG. 2B in page 4 and page 5 of U.S. Pat. No. 6,146,355 (Steerable catheter, Patent document 1).

In FIG. 2, the catheter of patent document 1 is illustrated.

According to the technology, the doctor in charge removes a tailbone side of a patient and inserts the shaft of the catheter 1 into a spine of the patient by controlling the catheter by using the driving device through the removed tailbone side such that drugs are supplied to a desired location or treat the patient by applying stimulus to the disk by transversely rotating a front end of the shaft.

However, in this case, during the treatment, the size or shape of the path, through which the shaft 2 is inserted, varies according to the movement of the patient or the physical state of the patient, so a possibility of malpractice is high.

Therefore, an endoscope catheter, which may separately identify an internal state, is inserted along with a catheter having the shaft rotated by the wire (3), however, because two catheters are inserted into a narrow space, moving the shaft is difficult, and rotating the front end of the treatment catheter to stimulate or supply drugs is difficult.

Figure 3:
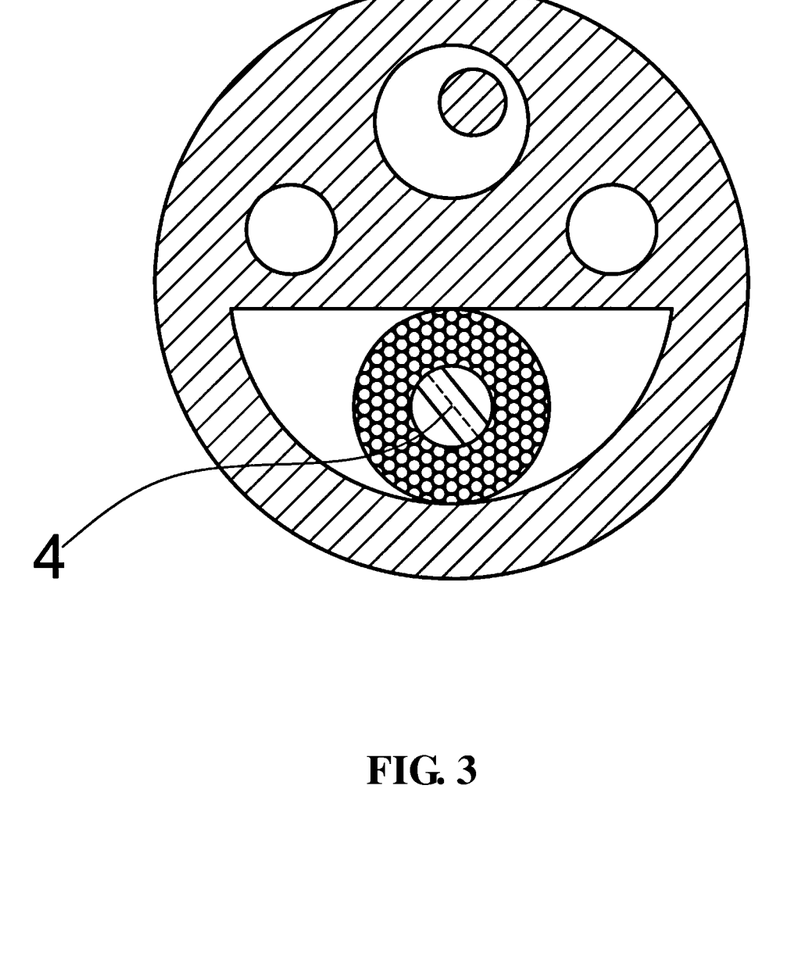
FIG. 3 is a cross sectional view illustrating a cross section of a shaft of the typical catheter.

To solve the problems, a catheter having a hole into which an optical fiber 4 is inserted, a hole into which a camera is inserted and a hole into which the wire to rotate the shaft front end is disclosed in FIG. 5 of page 4 of U.S. Pat. No. 5,396,880 (Endoscope for direct visualization of the spine and epidural space, Patent document 2).

In FIG. 3, a cross section of the catheter of patent document 2 is illustrated.

However, according to the technology, when a hole to inject the drug is formed, at least five holes are required, so the diameter of the shaft becomes larger, and when the diameter of the shaft becomes larger, the catheter is not appropriate for a procedure in which the shaft is inserted into a narrow space such as for the disk treatment.

In addition, in the process of bending the front end of the shaft according the movement of the wire, the integrated camera may not appropriately move together to photograph the internal part of the body, and to solve this problem, a connecting part to connect the camera to the shaft is required, but the diameter of the shaft becomes larger so the catheter is inappropriate.

As related arts, there is U.S. Pat. No. 6,146,355 (2000.11.14, Patent document 1).

DISCLOSURE

Technical Problem

A catheter using an optical fiber and a camera of the present invention is provided to solve the problem occurring in the related art, and an object of the present invention is to minimize a diameter of a shaft while forming a camera, an optical fiber, a wire and a hole to inject a drug in the shaft.

Specifically, the catheter includes a cap, to which front ends of the camera, the optical fiber and a drug injecting tube are inserted, and the wire is inserted into the cap such that the front ends of the camera, the optical fiber and a drug injecting tube are driven together according to a drive of the wire to accurately photograph the internal part, irradiate light and inject the drug.

In addition, the camera can be securely inserted into the cap without a separate connecting part and a fixed state can be maintained by the wire.

Further, the camera, the optical fiber and the drug injecting tube can be easily installed to the cap.

Furthermore, the front end of the wire can be configured to be separable such that the cap can be easily separated.

Technical Solution

To solve the problems described above, the catheter using an optical fiber and a camera of the present invention includes a shaft formed therein with a hollow part lengthwise along the shaft, including a flexible material, and having a cylindrical shape;

a cap including a head part having a same external diameter as an external diameter of the shaft, an inserting part integrally coupled to a side of the head part and having an external diameter identical to an internal diameter of the shaft such that the inserting part is inserted into an inner circumference of the shaft, a camera inserting groove having a cross sectional shape of U from an end of the head part to an end of the inserting part such that the camera inserting groove is concaved toward a center of the inserting part, and having a depth corresponding to ½ to ⅔ based on a diameter of the inserting part, a wire inserting hole transversely and straightly formed through the center of the inserting part while being spaced apart from an end of the head part, and having both ends to communicate with an outer circumference of the inserting part and an inner part to communicate with the camera inserting groove, a wire guide groove having a concave shape formed from both ends of the wire inserting hole to an end of the inserting part, and a lighting inserting groove and an injecting tube inserting groove which are spaced apart from each other and having a cross sectional shape of U from an end of the head part to the end of the inserting part; a wire having an insertion part to pass through the wire inserting hole and a longitudinal part formed along the wire guide groove while being coupled to the insertion part and having an outer circumference in contact with or spaced apart from the inner circumference of the shaft; a camera inserted into the camera inserting groove in such a manner that one end of the camera is aligned in line with the end of the head part and an opposite end of the camera does not reach the wire inserting hole, in which one side of an outer circumference of the camera makes contact with an inner surface of a center part of the camera inserting groove; a camera cable coupled to the camera and having a diameter smaller than a diameter of the camera to form a wire installation space between an inner surface of the camera inserting groove and the camera cable; an optical fiber having one side inserted into the lighting inserting groove and an opposite side installed along the hollow part in the shaft; a drug injecting tube having one side inserted into the injecting tube inserting groove and an opposite side installed along the hollow part in the shaft; a case to which an opposite end of the shaft is coupled; and a driving device installed in the case and connected to the wire to pull or release the wire to rotate a front end of the shaft and the cap inserted into the front end of the shaft.

In this case, the camera inserting groove formed in the cap may have a depth such that the camera inserting groove reaches an end of the insertion part of the wire, and the outer circumference of the longitudinal part of the wire may make contact with and adheres to an inner surface of the shaft.

In addition, one side of the camera may reach the inserting part of the cap, and one side of an outer circumference of the camera may make contact with the inner circumference of the shaft.

Further, a length of the camera may be identical to a length of the head part, an opposite side of the outer circumference of the camera may be aligned in line with an outer circumference of the shaft, and the opposite side of the outer circumference of the camera cable may make contact with and adheres to the inner surface of the shaft.

Accordingly, the longitudinal part of the wire may include a coupling part and a first longitudinal part, wherein one side of the coupling part is integrally coupled with the insertion part, and an opposite side of the coupling part is fixed to or separated from the first longitudinal part.

In addition, the camera cable and the optical fiber may protrude out of the case by passing through an inside of the case and may be connected to a control device, which includes a central processing unit and is connected to an input device and a display device, such that the camera cable and the optical fiber operate according to a drive of the control device.

Advantageous Effects

According to the present invention, by forming a hole for a camera, an optical fiber, a wire and a hole to inject a drug in the shaft, a diameter of the shaft can be minimized.

Specifically, the catheter includes a cap, to which front ends of the camera, the optical fiber and a drug injecting tube are inserted, and the wire is inserted into the cap such that the front ends of the camera, the optical fiber and a drug injecting tube are identically driven together according to a drive of the wire to accurately photograph the internal part, irradiate light and inject the drug.

In addition, the camera is solidly inserted to the cap without a separate connecting part and a fixed state is maintained by the wire.

In addition, the camera, the optical fiber and the drug injecting tube are easily installed to the cap. Furthermore, the front end of the wire is configured to be separable such that the cap is easily separated.

BEST MODE

Hereinafter, a catheter using an optical fiber and a camera is described in detail with reference to the accompanying drawings.

The catheter of the present invention includes a shaft 10, a cap 20, a wire 30, a camera 40, a camera cable 41, a drug injecting tube 50, an optical fiber 60, a case 70 and a driving device 80.

Figure 4:
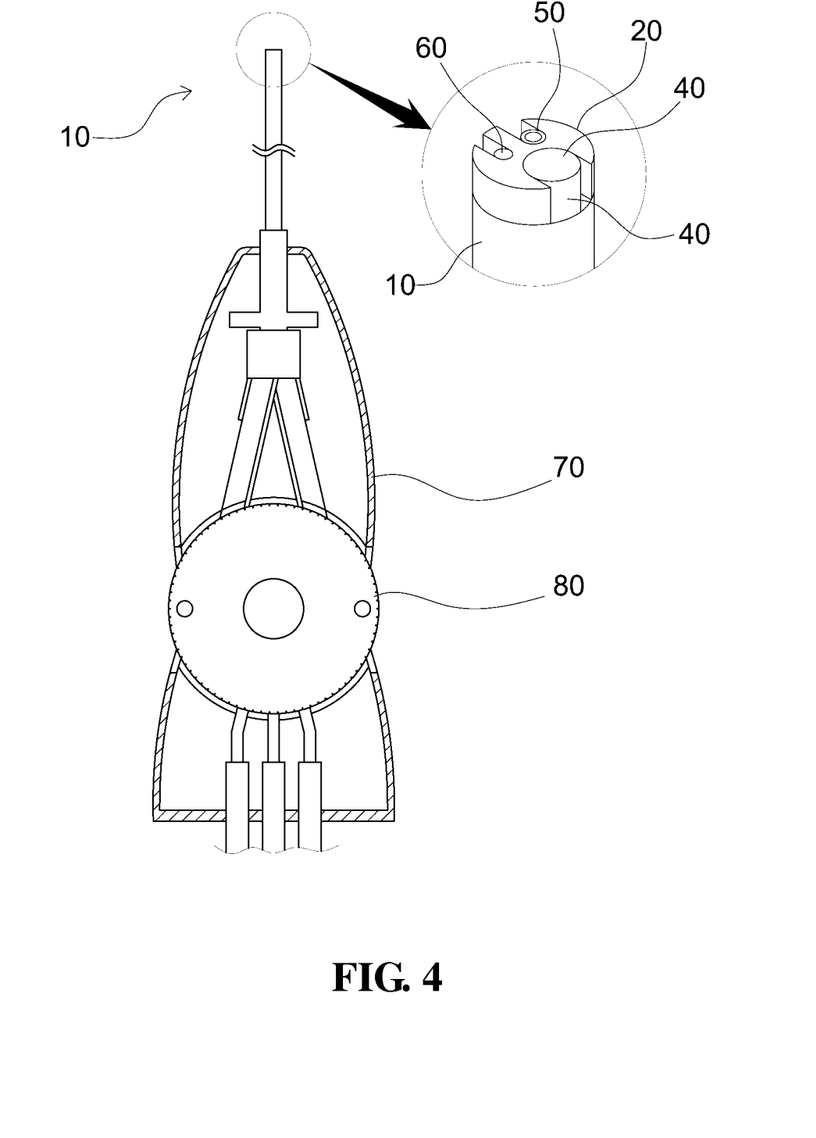
FIG. 4 is a schematic view illustrating the catheter according to an embodiment of the present invention.
Figure 5:
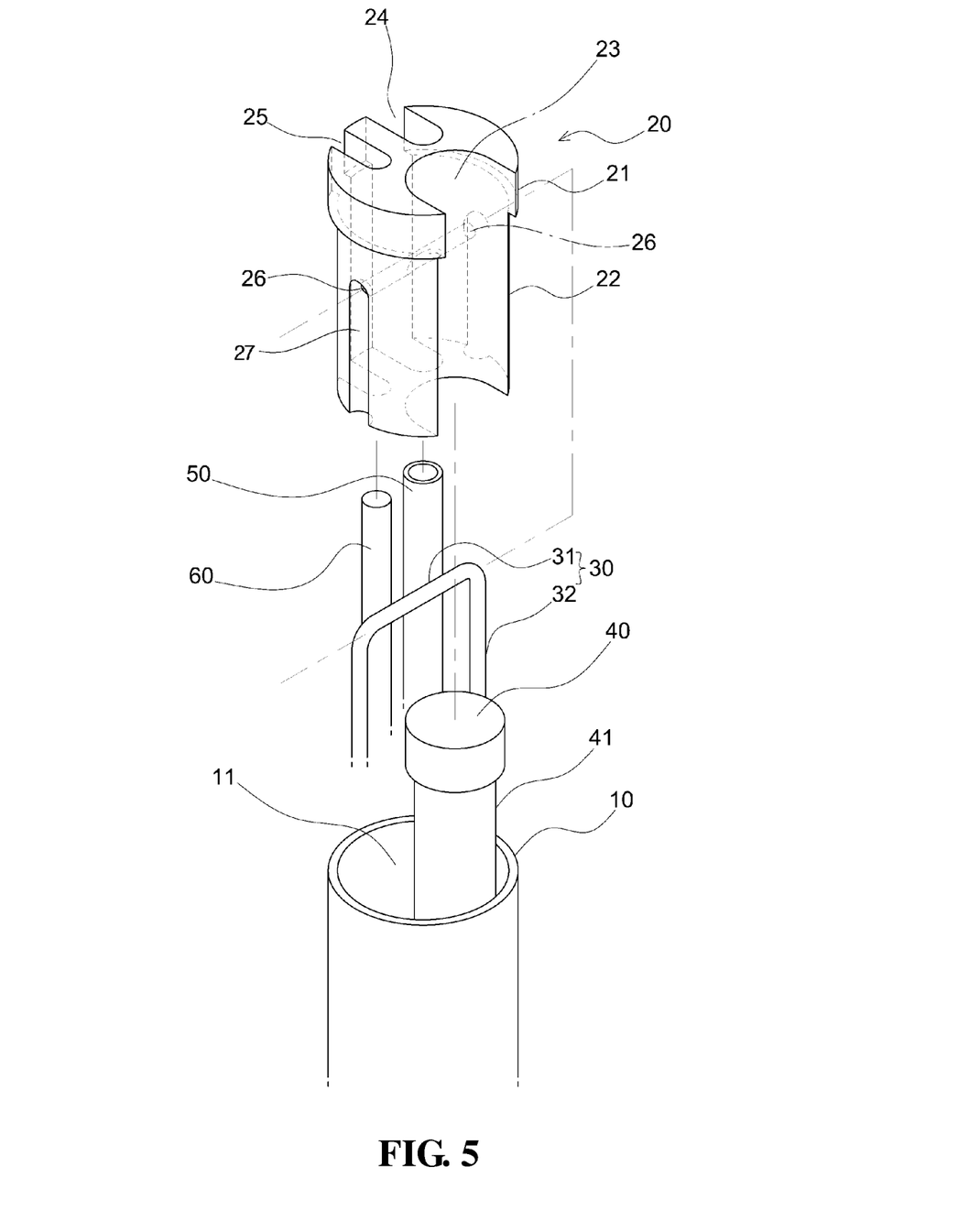
FIG. 5 is an explosive perspective view illustrating a cap installing part of the catheter according to an embodiment of the present invention.

The shaft 10, as illustrated in FIG. 4 and FIG. 5, is formed therein with a hollow part 11 lengthwise along the shaft 10, including a flexible material and having a cylindrical shape.

The cap 20, which is an important component of the present invention, as illustrated in FIG. 4 and FIG. 5, includes a head part 21 having a same external diameter as an external diameter of the shaft 10, and an inserting part 22 integrally coupled to a side of the head part 21 and having an external diameter identical to an inner diameter of the shaft 10 and inserted and fitted in an inner circumference of the shaft 10.

The outer diameter of the head part 21 may be slightly greater than the outer diameter of the shaft 10, however, the diameters are preferably formed to be same.

The cap 20, as illustrated, includes a camera inserting groove 23 having a cross sectional shape of U from an end of the head part 21 to an end of the inserting part 22 such that the camera inserting groove 23 is concaved toward a center of the inserting part 22.

Figure 6:
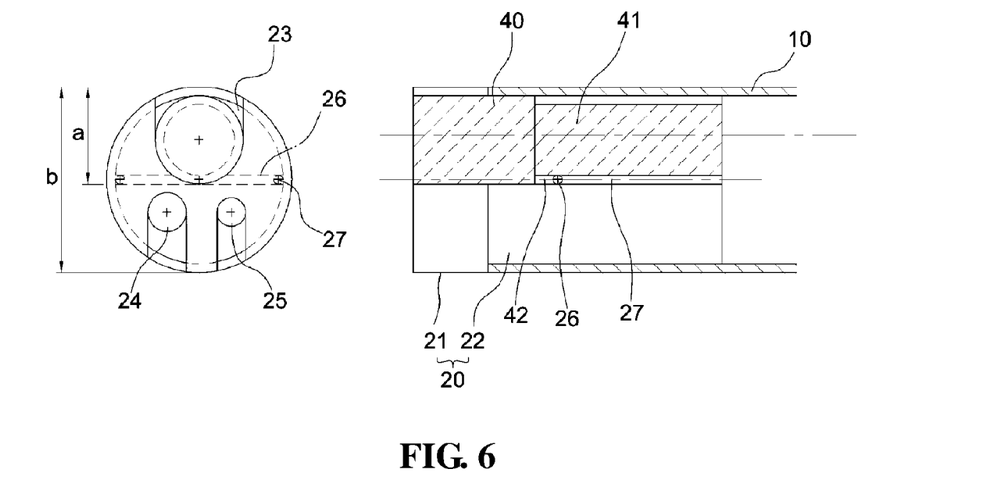
FIG. 6 and FIG. 7 are cross sectional view illustrating a camera according to an embodiment of the present invention.

The camera inserting groove 23, as illustrated in FIG. 6, when based on the inserting part 22, preferably has a depth corresponding to ½ to ⅔ based on a diameter b of the inserting part 22.

In addition, the cap 20 includes a wire inserting hole 26 transversely and straightly formed through the center of the inserting part 22 while being spaced apart from an end of the head part 23, and having both ends to communicate with an outer circumference of the inserting part 22 and an inner part to communicate with the camera inserting groove 23, Further, a wire guide groove 27 having a concave shape formed from both ends of the wire inserting hole 26 to an end part of the inserting part 22 is formed.

In addition, the cap 20 includes a lighting inserting groove and an injecting tube inserting groove 24 which are spaced apart from each other and having a cross sectional shape of U from an end of the head part 21 to the end of the inserting part 22.

The wire 30 includes an insertion part 31 to pass through the wire inserting hole 26 and a longitudinal part 32 formed along the wire guide groove 27 while being coupled to the insertion part 31.

In this case, an outer circumference of the longitudinal part 32 preferably makes contact with or spaced apart from the inner circumference of the shaft 10.

Figure 7:
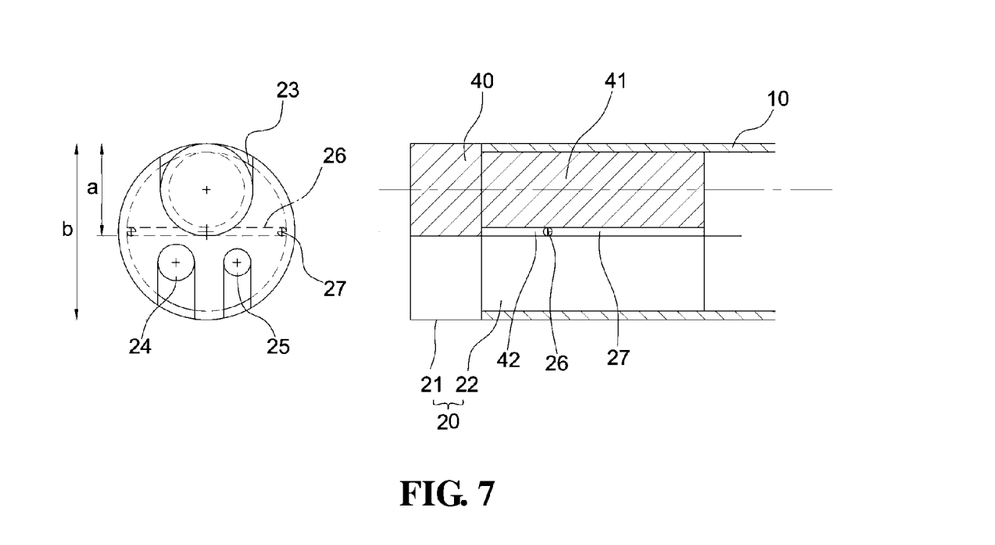

The camera (40) is inserted into the camera inserting groove 23, as illustrated in FIG. 6 and FIG. 7, in such a manner that one end of the camera 40 is aligned in line with the end of the head part 21.

In addition, the other side of the camera 40, as illustrated, does not reach the wire inserting hole (26).

An end of the other side of the camera 40 is latched by the insertion part 31 of the wire 30 such that the camera 40 is prevented from moving into the shaft 40.

In addition, the camera 40 has one side of an outer circumference making contact with an inner surface of a center part of the camera inserting groove 23 such that the camera 40 is prevented from moving into the camera inserting groove 23.

The camera cable (41), as illustrated, is coupled to the camera (40), has a diameter smaller than a diameter of the camera (40) to form a wire installation space (43) between an inner surface of the camera inserting groove (23) and the camera cable (41).

Forming the wire installation space 42 is very important.

When the one side of the outer circumference of the camera passes over a center of the shaft 10 because the diameter of the camera 40 is greater than the diameter of the shaft 10, normally, the wire 30 to drive the shaft 10 is uninstallable.

Specifically, when the wire 30 is fixed to both sides of the shaft 10, parts of the shaft 30, to which the wire is connected, are required to be opposite to each other based on the cross section of the shaft 10, however, when the size of the camera 40 becomes large, the two wires 30 may not be accurately positioned opposite to each other when the two wires 30 are connected in the shaft 10.

That is, when the large sized camera 40 is installed, two different wires 30 are required, and when the camera 40 cable, a drug injecting tube, a light providing tube, etc. are installed together with the wire 30 in the narrow shaft 10, interferences between each other occur when the shaft 10 is bent such that smooth operation is prevented.

However, because the diameters of the camera 40 and the camera cable 41 are different, as in the present invention, the wire 30 passes through an inside of the camera inserting groove 23 such that the diameter of the shaft 10 is not required to be increased, and the wire 30 is latched by a step between the camera 40 and the camera cable 41 such that the wire 30 and the cap are firmly coupled and the camera 40 is prevented from moving into the shaft 10.

In the configuration, the camera 40 includes a lens, and the camera cable 41 is installed for controlling the camera 40.

The optical fiber 60, as illustrated in FIG. 4 and FIG. 5, has one side inserted into the lighting inserting groove 25 and the other side installed along the hollow part 11 in the shaft 10.

The optical fiber 60 allows the camera to smoothly photograph by irradiating light at a front end of the shaft 10, and only the optical fiber is preferably used, however, a tube having an LED lamp at a front end may be used.

In addition, the optical fiber 60 preferably includes a flexible material and a light source at an end of the optical fiber 60.

The drug injecting tube 50 has one side inserted into the injecting tube inserting groove 24 and the other side installed along the hollow part 11 in the shaft 10.

The case 70 is coupled to an end of the other side of the shaft, and a driving device 80 to which the wire 30 is connected is installed in the case 70.

The driving device 80 is connected to the wire 30 to pull or release the wire 30 to rotate a front end of the shaft 10 and the cap 30 inserted into the front end of the shaft 10.

The driving device 80, as illustrated, is rotatable in a clockwise direction or a counter clockwise direction based on a central rotating shaft, and a spring may be installed in the rotating shaft so that the driving device 80 rotates to a prior position after rotating to one direction.

In addition, each of the wires 80 is fixed to left and right sides of the driving device 80, respectively, such that the wires 80 are wound around the driving device 80 when the driving device 80 is rotated in the left and right directions.

In the embodiment, both sides of the wires 30 are pulled or released according to the left and right rotations of the driving device 80 in such a manner that the shaft 10 is rotated in left and right directions.

The driving device 80 used in the present invention is not limited to the drawings and various typical driving devices 80 may be employed.

In the configuration described above, the camera inserting groove 23 formed on the cap 20, as illustrated in FIG. 6 and FIG. 7, has a depth such that the camera inserting groove 23 reaches an end of the insertion part 31 of the wire 30, and the outer circumference of the longitudinal part 32 of the wire 30 makes contact with and adheres to the inner surface of the camera inserting groove 23. The camera cable 41 adheres to the wire 20 such that space utilization is maximized, and the cap 20 in contact with the wire 30 is instantaneously bends without delay according to an operation of the driving device 80.

In addition, as illustrated, of the outer circumference of the longitudinal part 32 of the wire 30 makes contact with and adheres to the inner circumference of the shaft 10 such the front end of the shaft spontaneously bends without delay by a pull of the wire 30.

Meanwhile, a diameter of the camera 40, as illustrated in FIG. 6, is formed in such a manner that a side of the camera 40 reaches the inserting part 22 of the cap 20, a side of the outer circumference of the camera 40 makes contact with and adheres to the inner circumference of the shaft or, as illustrated in FIG. 7, the lengths of the camera 40 and the head part 21 are identical, the other side of the outer circumference of the camera 40 is aligned in line with a circumference of the shaft 10, and the other side of the outer circumference of the camera cable 41 makes contact with and adheres to the inner circumference of the shaft 10.

In the case of FIG. 7, the size of the camera 40 may be larger than the camera in FIG. 6.

In addition, in the case of FIG. 6, a gap between the front end of the camera 40 and the wire 40 is made narrower or in contact with each other such that the camera 40 may be better prevented from moving into the shaft 10.

Figure 8:
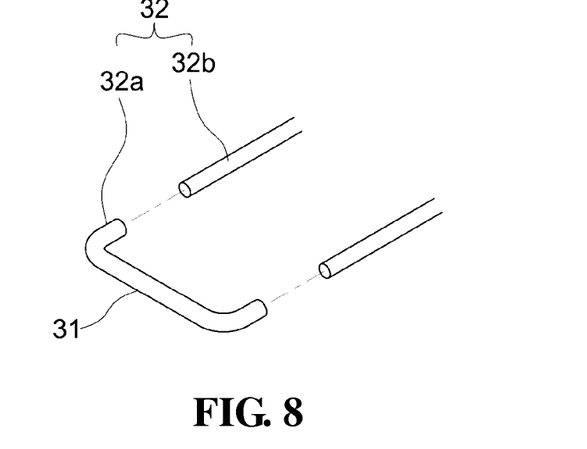
FIG. 8 is an explosive perspective view illustrating a wire according to an embodiment of the present invention.
Figure 9:
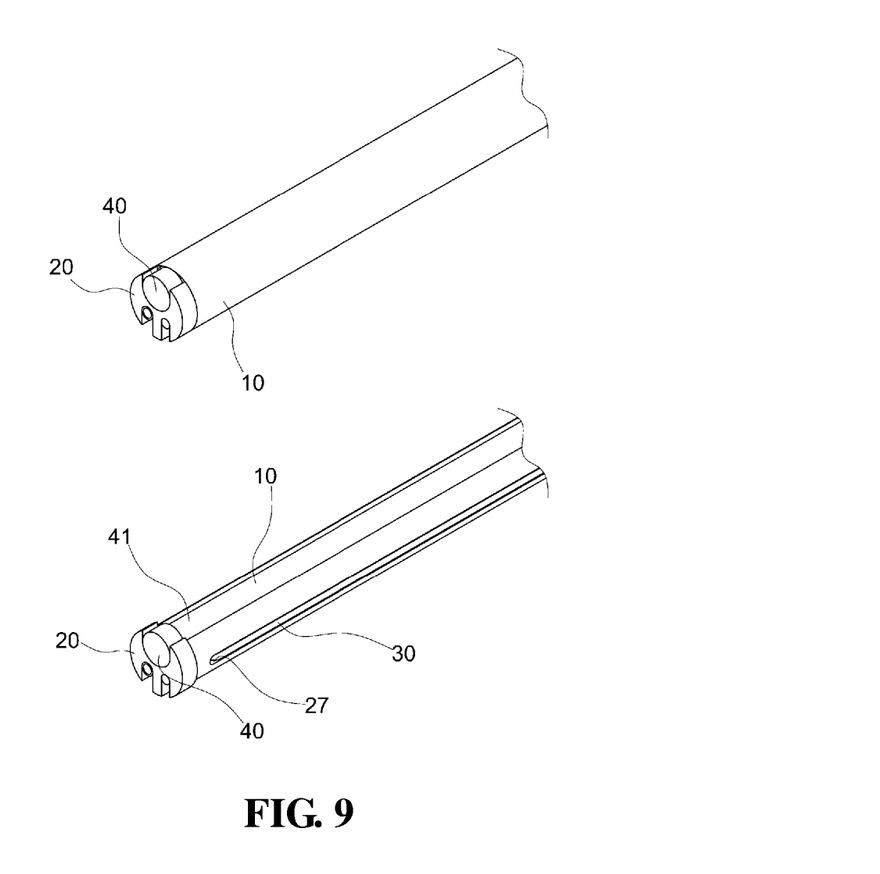
FIG. 9 is a perspective view illustrating states before and after the cap is installed according to an embodiment of the present invention.

Meanwhile, as illustrated in FIG. 8, the longitudinal part 32 of the wire 30 includes a connecting part 32a and a first longitudinal part 32b, wherein one side of the coupling part 32a is integrally coupled to the insertion part 31, and the other side of the coupling part 32a is fixed to or separated from the first longitudinal part 32b.

To this end, the connecting part 32a is formed in a tube shape, and the first longitudinal part 32b is inserted and fitted into the connecting part 32a, and when the wire 30 is separated, as described, the cap 20 can be easily separated for repair or cleaning.

Figure 10:
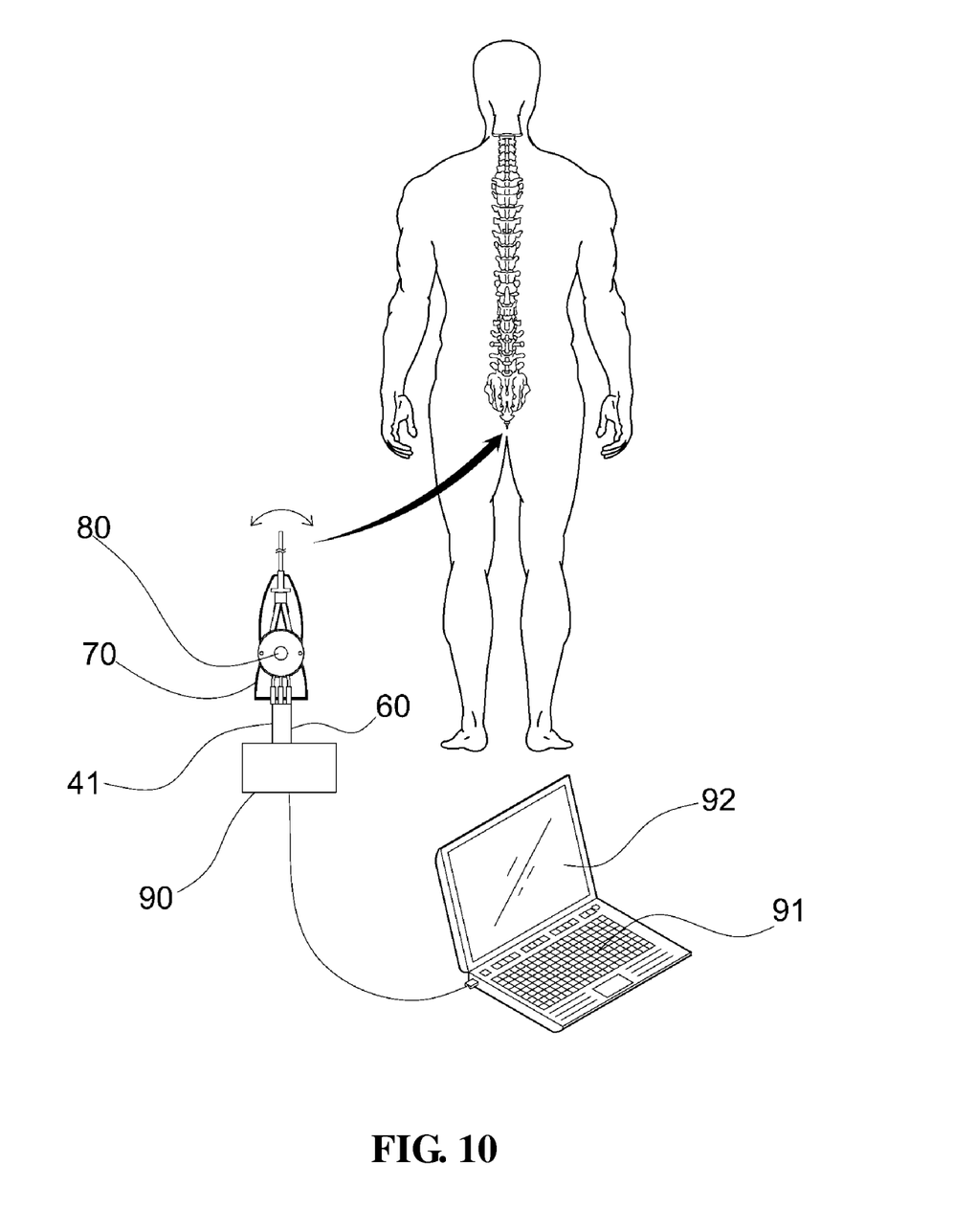
FIG. 10 is a schematic view illustrating when a control device is added according to an embodiment of the present invention.

In the catheter of the present invention, as illustrated in FIG. 10, the camera cable 41 and the optical fiber 6 protrude out of the case 70 by passing through an inside of the case 70 and are connected to a control device 90, which includes a central processing unit and is connected to an input device 91 and a display device 92, such that the camera cable 41 and the optical fiber 6 operate according to a drive of the control device 90.

In FIG. 10, a separate view box is configured as the control device 90, an example of the view box connected a laptop having a keyboard and a screen by utilizing a USB cable, etc. is illustrated, and in this case, the catheter is controlled through a program stored in the laptop and a mechanical control is controlled through the view box.

However, configurations of the control device 90 are not limited to the examples, and may be performed by utilizing typical control and communication technologies.

In addition, in the configuration described above, the camera inserting groove 23, the lighting inserting groove 25, and the injecting tube inserting groove 24 are formed in a groove shape instead of a hole shape such that installations and separations of the camera 40, the optical fiber 60 and the drug injecting tube 50 are easily performed.

The catheter of the present invention is capable of lighting and photographing, rotating the shaft, and furthermore, minimizing the diameter of the catheter even though the camera 40, the optical fiber 60, the wire 30 and the drug injecting tube 50 are installed.

The catheter of the present invention can be employed in various endoscope operations, and specifically, has excellent effects for use in intervertebral disk treatments.

The invention claimed is:

1. A catheter comprising:
   a shaft formed therein with a hollow part lengthwise along the shaft, and having a cylindrical shape;
   a cap comprising:
      a head part having a same external diameter as an external diameter of the shaft, wherein the head part has a top end of the head part and a bottom end of the head part,
      an inserting part integrally coupled to the head part and having an external diameter identical to an internal diameter of the shaft such that the inserting part is inserted into an inner circumference of the shaft, wherein the insertion part has a top end of the insertion part and a bottom end of the insertion part,
      a camera inserting groove having a cross sectional shape of U from the top end of the head part to the bottom end of the inserting part such that the camera inserting groove is concaved toward a center of the inserting part, and having a depth of at least 50% of a diameter of the inserting part and not greater than 67% of the diameter of the inserting part,
      a wire inserting hole transversely and straightly formed through the center of the inserting part while being spaced apart from the bottom end of the head part, having both ends of the wire inserting hole communicating with an outer circumference of the inserting part, and having an inner part of the wire inserting hole communicating with the camera inserting groove,
      a wire guide groove having a concave shape formed from both ends of the wire inserting hole to the bottom end of the inserting part, and
      a lighting inserting groove and an injecting tube inserting groove which are spaced apart from each other and each having a cross sectional shape of U from the top end of the head part to the bottom end of the inserting part;
   a wire having an insertion part formed to pass through the wire inserting hole, and having a longitudinal part formed along the wire guide groove while being coupled to the insertion part, wherein an outer circumference of the longitudinal part is in contact with the inner circumference of the shaft;
   a camera having a bottom end of the camera and a top end of the camera, wherein the camera is inserted into the camera inserting groove in such a manner that the top end of the camera is flush with the top end of the head part, wherein the bottom end of the camera does not reach the wire inserting hole, and wherein one side of an outer circumference of the camera makes contact with an inner surface of a center part of the camera inserting groove;
   a camera cable coupled to the camera and having a diameter smaller than a diameter of the camera to form a wire installation space between an inner surface of the camera inserting groove and the camera cable;
   an optical fiber having a top portion inserted into the lighting inserting groove and having a lower portion installed along the hollow part in the shaft;
   a drug injecting tube having a top portion inserted into the injecting tube inserting groove and having a lower portion installed along the hollow part in the shaft;
   a case to which a bottom end of the shaft is coupled; and
   a driving device installed in the case, connected to the wire, and configured to pull or release the wire to rotate a top end of the shaft and the cap inserted into the top end of the shaft.

2. The catheter according to claim 1, wherein the outer circumference of the longitudinal part of the wire contacts an inner surface of the shaft.

3. The catheter according to claim 2, wherein the bottom end of the camera is below the top end of the inserting part, and wherein one side of an outer circumference of the camera makes contact with the inner circumference of the shaft such that a portion of the camera is within the shaft.

4. The catheter according to claim 2, wherein the bottom end of the camera is coplanar with the bottom end of the head part, and wherein an external portion of an outer circumference of the camera is aligned with an outer circumference of the shaft such that the camera is partially seated on a top surface of the shaft, and wherein an internal portion of the outer circumference of the camera cable contacts or almost contacts the inner surface of the shaft.

5. The catheter according to claim 3, wherein the longitudinal part of the wire includes a coupling part and a first longitudinal part, wherein one side of the coupling part is integrally coupled with the insertion part, and an opposite side of the coupling part is fixed to or separated from the first longitudinal part.

6. The catheter according to claim 2, wherein the camera cable and the optical fiber protrude out of the case by passing through an inside of the case, and are connected to a control device, which includes a central processing unit and is connected to an input device and a display device, such that the camera cable and the optical fiber operate according to a drive of the control device.

7. The catheter according to claim 4, wherein the longitudinal part of the wire includes a coupling part and a first longitudinal part, wherein one side of the coupling part is integrally coupled with the insertion part, and an opposite side of the coupling part is fixed to or separated from the first longitudinal part.

8. A catheter comprising:
- a shaft formed therein with a hollow part lengthwise along the shaft, and having a cylindrical shape;
- a cap comprising:
  - a head part having a same external diameter as an external diameter of the shaft, wherein the head part has a top end of the head part and a bottom end of the head part,
  - an inserting part integrally coupled to the head part and having an external diameter identical to an internal diameter of the shaft such that the inserting part is inserted into an inner circumference of the shaft, wherein the insertion part has a top end of the insertion part and a bottom end of the insertion part,
  - a camera inserting groove having a cross sectional shape of U from the top end of the head part to the bottom end of the inserting part such that the camera inserting groove is concaved toward a center of the inserting part, and having a depth of at least 50% of a diameter of the inserting part and not greater than 67% of the diameter of the inserting part,
  - a wire inserting hole transversely and straightly formed through the center of the inserting part while being spaced apart from the bottom end of the head part, having both ends of the wire inserting hole communicating with an outer circumference of the inserting part, and having an inner part of the wire inserting hole communicating with the camera inserting groove,
  - a wire guide groove having a concave shape formed from both ends of the wire inserting hole to the bottom end of the inserting part, and
  - a lighting inserting groove and an injecting tube inserting groove which are spaced apart from each other, and each having a cross sectional shape of U from the top end of the head part to the bottom end of the inserting part;
- a wire having an insertion part formed to pass through the wire inserting hole, and having a longitudinal part formed along the wire guide groove while being coupled to the insertion part, wherein an outer circumference of the longitudinal part is in contact with the inner circumference of the shaft;
- a camera having a bottom end of the camera and a top end of the camera, wherein the camera is inserted into the camera inserting groove in such a manner that the top end of the camera is flush with the top end of the head part, wherein the bottom end of the camera does not reach the wire inserting hole, and wherein one side of an outer circumference of the camera makes contact with an inner surface of a center part of the camera inserting groove; and
- a camera cable coupled to the camera and having a diameter smaller than a diameter of the camera to form a wire installation space between an inner surface of the camera inserting groove and the camera cable.

* * * * *